United States Patent [19]

Fong et al.

[11] Patent Number: 4,994,620

[45] Date of Patent: Feb. 19, 1991

[54] AMINES FOR ALCOHOLS

[75] Inventors: Pak Y. Fong; Kim R. Smith; Joe D. Sauer, all of Baton Rouge, La.

[73] Assignee: Ethyl Corporation, Richmond, Va.

[21] Appl. No.: 195,883

[22] Filed: May 19, 1988

Related U.S. Application Data

[63] Continuation-in-part of Ser. No. 133,733, Dec. 16, 1987, which is a continuation-in-part of Ser. No. 79,522, Jul. 30, 1987, abandoned, which is a continuation-in-part of Ser. No. 22,095, Mar. 5, 1987, abandoned.

[51] Int. Cl.$^5$ .................. C07C 209/26; C07C 209/16
[52] U.S. Cl. ..................................... 564/473; 564/479
[58] Field of Search ........................ 564/473, 479, 480

[56] References Cited

U.S. PATENT DOCUMENTS

| | | | |
|---|---|---|---|
| 1,762,742 | 6/1930 | Reppe | 564/473 |
| 2,609,394 | 9/1952 | Davies et al. | 564/473 |
| 4,182,915 | 1/1980 | Harvey | 568/735 |
| 4,210,605 | 7/1980 | Hoshino et al. | 260/585 |
| 4,229,374 | 10/1980 | Slaugh et al. | 564/479 |
| 4,254,060 | 3/1981 | Kimura et al. | 564/479 |
| 4,310,697 | 1/1982 | Cheminal et al. | 564/479 |
| 4,409,399 | 10/1983 | Swift et al. | 564/480 |
| 4,683,336 | 7/1987 | Blackhurst | 564/480 |

FOREIGN PATENT DOCUMENTS

| | | | |
|---|---|---|---|
| 0042345 | 3/1984 | Japan | 564/473 |
| 0106441 | 6/1984 | Japan | 564/480 |

*Primary Examiner*—Glennon H. Hollrah
*Assistant Examiner*—Susan P. Treanor
*Attorney, Agent, or Firm*—Joseph D. Odenweller; Patricia J. Hogan

[57] ABSTRACT

Alkylamines such as methylamine and dimethylamine react with alcohols and aldehydes at 150°–275° C. in the presence of hydrogen and a catalyst initially consisting essentially of (1) a copper compound selected from copper carbonate, copper oxide, copper hydroxide or mixtures thereof, (2) a zinc compound selected from zinc carbonate, zinc oxide, zinc hydroxide or mixtures thereof and (3) a metal compound selected from carbonates, oxides and hydroxides of a Group IIA metal and mixtures thereof at least one of said copper compound and zinc compound being a carbonate. Conversions and yields are high and the amount of heavy by-product is low.

20 Claims, No Drawings

AMINES FOR ALCOHOLS

This application is a continuation-in-part of application Ser. No. 133,733 filed Dec. 16, 1987 now pending which in turn is a continuation-in-part of applications Ser. No., 079,522 filed July 30, 1987 now abandoned and Ser. No(s)., 022,095 and 022,047, both filed March 5, 1987 both now abandoned.

BACKGROUND

It has long been known that alcohol can react with ammonia or primary or secondary amines to replace one or more hydrogen atoms bonded to nitrogen with the alkyl residue of the alcohol. The reaction is promoted by catalysts. Use of a supported oxygen compound of phosphorus is reported in U. S. 2,073,671. Another process is described in U. S. 2,160,058 using copper-barium-chromium oxides, copper-chromium oxides or copper-aluminum oxides. Reaction of ethylene glycol with ammonia using a catalyst such as nickel-aluminum, nickel-silicon, nickel, copper, copper-chromium, copper-zinc-chromium, thorium, magnesium, molybdenum or osmium oxides is said to form alkoxy amines according to U. S. 2,160,058. Reaction of an alcohol with ammonia or an amine in the presence of hydrogen using an alumina or silica supported cobalt-nickel-copper-catalyst is described in U.S. 4,014,933. Hoshino et al. U. S. 4,210,605 describe a process for making aliphatic amines by reacting an aliphatic alcohol or aldehyde with ammonia or a primary or secondary amine using a homogenous colloidal catalyst formed by dissolving a copper or silver salt of a fatty acid in alcohol and reducing the metal. Optionally the solution can contain a Group VIII metal carboxylate or a manganese or zinc metal carboxylate. It can also contain an alkali metal or alkaline earth metal carboxylate. The catalyst formed is a homogenous colloid that cannot be separated by filtration. In contrast the present catalyst is a solid catalyst that can be removed by filtration and recycled.

More recently, U. S. 4,409,399 describes the alkylation of ammonia or a primary or secondary amine using as the catalyst an unsupported copper oxide or hydroxide, nickel oxide or hydroxide and optionally a Group IIA metal oxide or hydroxide. Similarly Blackhurst U. S. 4,683,336 describes an amination process which uses a copper carbonate-nickel carbonate catalyst which may optionally contain cobalt carbonate.

One of the problems encountered when making long-chain alkyl di-lower alkylamines such as $C_{8-22}$ alkyl dimethylamines by the reaction of a long-chain alcohol with a di-lower alkylamine is that any unreacted long-chain alcohol remaining in the reaction mixture will boil at about the same temperature as the desired product which makes purification very difficult. Hence, it is essential that conversion of alcohol be essentially complete, e.g., at least 95%, to have a commercially viable process when making an amine such as a $C_{8-22}$ alkyl dimethylamine. Likewise it is essential that disproportionation to form long-chain alkylamine and/or long-chain alkyl mono-lower alkylamine be minimized as these primary and secondary amines are also extremely difficult to separate from the desired long-chain alkyl di-lower alkylamine product.

Another problem with the catalytic route to trialkylamine is that such processes can form by-products such as alkanamides of the amines and alkyl alkanoate esters from the alcohol. Also when attempting to make a long-chain alkyl dilower-alkylamine, alkyl interchange can occur to give di-long-chain alkyl mono-lower alkylamine. These reactions lower the yield and also form by-products having a high molecular weight such that they remain in the trialkylamine products unless the entire product is rectified and even then separation can be difficult.

SUMMARY OF THE INVENTION

It has now been discovered that trialkylamines can be made in high yield with low amounts of heavy by-products by reacting an alcohol or aldehyde with a mono- or di-alkylamine at 150°–275° C. in the presence of hydrogen and a catalyst initially consisting essentially of (1) a copper compound selected from copper carbonate, oxide or hydroxide, (2) a zinc compound selected from zinc carbonate, oxide or hydroxide and (3) a metal compound selected from carbonates, oxides and hydroxides of Group IIA metals such that at least a portion of the copper compound or zinc compound is initially in the form of a carbonate. The catalyst may be supported or unsupported.

DESCRIPTION OF THE PREFERRED EMBODIMENTS

A preferred embodiment of the invention is a process for making a trialkylamine by reacting an alcohol or aldehyde with mono- or di-alkylamine at 150°–275° C. in the presence of hydrogen and in contact with a catalyst initially consisting essentially of (1) a copper compound selected from copper carbonate, copper oxide or copper hydroxide or mixtures thereof, (2) a zinc compound selected from zinc carbonate, zinc oxide or zinc hydroxide or mixtures thereof and (3) a metal compound selected from carbonates, oxides and hydroxides of Group IIA metals or mixtures thereof, at least a portion of at least one of said copper compound and zinc compound being a carbonate.

The process can be conducted by forming a mixture of the alcohol and an alkylamine or dialkylamine containing the catalyst and stirring the mixture at reaction temperature, optionally but preferably while contacting the mixture with hydrogen. In practice the hydrogen can be sparged into the liquid phase and the off-gas, consisting mainly of hydrogen, passed through a condenser to condense water and other volatiles which co-distill. The hydrogen can then if desired be recirculated to the reaction mixture. Any amine or alcohol lost in the vent stream can be made-up by adding additional alcohol or amine.

The reaction temperature can vary widely. The temperature should be high enough to cause the reaction to proceed at a reasonable rate but not so high as to cause decomposition of reactants or products. A useful temperature range in which to experiment is about 150°–300° C. A preferred temperature is 150°–275° C. A more preferred temperature range is about 180°–250° C. Excellent results have been achieved in the range of 190°–230° C.

The reaction can be conducted at atmospheric pressure or above or below atmospheric pressure. Best results have been achieved operating at atmospheric pressure. However, if pressure is required to reach the desired alkylation temperature or to increase the amount of amine in the reaction mixture, then such pressure can be applied. When operating under pressure it is still preferred to sparge hydrogen through the liquid phase and to vent the vapor phase through a pressure regulating valve.

The alcohols or aldehydes used in the process are preferably terminal alcohols or aldehydes or mixtures thereof. Examples of such alcohols are methanol, ethanol, n-propanol, 1-butanol, isobutanol, 1-pentanol, 1-hexanol, 2-ethyl-l-hexanol, 4-methyl-1-decanol, 1-dodecanol, 2-ethyl-1-tetradecanol, 1-eicosanol, 1-docosanol, 2-ethyl-1-eicosanol and the like.

Examples of terminal aldehydes are propanal, butanal, 2-ethylhexanal, dodecanal octadecanal, eicosanal and the like.

Use of alcohols in the process is preferred. The preferred alcohols are mainly linear terminal alcohols. By "mainly terminal" is meant at least 80 weight percent terminal. When reacting with a di-lower alkylamine, e.g., a di-$C_{1-2}$ alkylamine, the more preferred alcohols are mainly linear terminal alcohols containing 8–22 carbon atoms, still more preferably 10–18 carbon atoms and most preferably 12–14 carbon atoms. When the alkylamine is a mono-lower alkylamine, e.g. a mono-$C_{1-2}$ alkylamine, the more preferred alcohols contain 6–20 carbon atoms, still more preferably 8–14 carbon atoms and most preferably 10–12 carbon atoms.

Examples of the above linear alcohols are 1-hexanol, 1-octanol, 1-decanol, 1-dodecanol, 1-tetradecanol, 1-hexadecanol, 1-octadecanol, 1-eicosanol and 1-docosanol.

The process can be used to alkylate the nitrogen atom of any primary or secondary amine. Examples of these are alkylamines, cycloalkylamines, aralkylamines, arylamines, dialkylamines, diaralkylamines, aralkyl alkylamines, alkylarylamines and the like such as methylamine, dimethylamine, ethylamine, methylethylamine, diethylamine, butylamine, 2-ethyl hexylamine, dibutylamine, cyclohexylamine, dicyclohexylamine, benzylamine, dibenzylamine, aniline, toluidine and the like.

Examples of primary lower alkylamines include methylamine, ethylamine, 1-propylamine, isobutylamine, 1-butylamine and the like. Preferred mono-lower-alkylamines are those in which the alkyl group contains about 1–8 carbon atoms and more preferably 1–4 carbon atoms, especially methylamine.

Examples of secondary amines include dimethylamine, diethylamine, di-n-butylamine, didecylamine, di(2-ethyldecyl)amine, dioctadecylamine, methyl dodecylamine, methyl eicosylamine, methyl docosylamine, methyl triacontylamine, isobutyl 2-ethylhexyl amine, n-butyl hexadecylamine, ethyl nonylamine, ethyl tetradecylamine, methyl cyclohexylamine, ethyl cyclohexylamine, piperazine, piperidine, N-methyl aniline, N,N'-di-methyl phenylene diamine, morpholine, and the like. The preferred secondary amines are the di-lower alkylamines such as the di-$C_{1-4}$ alkylamines. The most preferred secondary amines are di-$C_{1-2}$ alkylamines, especially dimethylamine ("DMA").

The ratio of alcohol to amine can vary within a wide range. With a dialkylamine the stoichiometry requires one mole of alcohol per mole of dialkylamine. With a monoalkylamine the stoichiometry requires two moles of alcohol per mole of amine. The process is usually conducted by placing the alcohol or aldehyde and catalyst in a reactor and feeding the amine to the alcohol or aldehyde while passing hydrogen through the liquid phase. With lower amines such as methylamine and dimethylamine, the reaction temperature is above the normal amine boiling point of the amines. With these volatile amines the process is readily conducted by sparging amine in a vapor state and hydrogen into the liquid alcohol containing the catalyst and continuously venting the system to remove unreacted amine, hydrogen and water formed in the reaction. Hydrogen and amine can be recycled if desired.

When using a higher alcohol and a lower dialkylamine such as dimethylamine, it is preferred to have the amine in large excess so that all or almost all of the alcohol is consumed. This is because the higher alcohols are very difficult to separate from the higher alkyl di-lower alkylamines. A useful range is about 1.1–20 moles of di-lower alkylamine per mole of higher (e.g. $C_{8-22}$) alcohol. In practice the di-lower alkylamine in the vapor phase, preferably in combination with hydrogen, is continuously injected into the heated liquid reaction mixture. The di-lower alkylamine that does not react with the alcohol can be recovered from the vent gas and reinjected until substantially all (e.g., at least 95 percent) of the alcohol is converted.

When making a di-higher alkyl-mono-lower-alkylamine, e.g. di-$C_{6-20}$ alkyl methylamine, the ratio of alcohol or aldehyde to mono-lower-alkylamines should be high enough to dialkylate all or almost all of the initial mono-lower-alkylamine. An efficient way to conduct the process is to feed monoalkylamine until the mole ratio of alcohol to amine feed is about 1.8–2.5:1. The monoalkylamine addition can be discontinued and one can proceed to monitor the reaction composition using gas chromatography (GC) as the reaction proceeds. If it is seen that the alcohol is consumed while substantial amounts of mono- and/or di-alkylamine remain, then more alcohol can be added to convert the mono- and/or di-alkylamine to trialkylamine. If on the other hand the amines in the reaction mixture are all or almost all trialkylamines while unreacted alcohol or aldehyde remains, then additional monoalkylamine can be added to react with this alcohol or aldehyde. The stoichiometric ratio for the reaction is 2 moles of alcohol or aldehyde per mole of alkylamine but the amount of alcohol, aldehyde and amine actually fed or added to the reaction may vary somewhat from this ideal ratio due to factors such as monoalkylamine being lost in the vent gas.

The reaction is conducted for a period of time adequate to achieve the desired degree of alkylation. The reaction is usually complete in about 1–24 hours. A preferred reaction time is about 2–12 hours. Under the most preferred reaction conditions the reaction is essentially complete in about 4–10 hours.

The catalyst or mixture of catalysts used in the reaction contains the elements copper, zinc and a Group IIA metal. The catalyst may be supported or unsupported. Minor amounts of other metals may be present as long as they do not interfere with the catalytic action of the Cu-Zn -Group IIA metal. The presence of any other catalytic metal is unnecessary.

By "at least part" we mean at least 50 weight percent and preferably at least 80 weight percent of the copper and/or zinc compounds.

In our earlier application Serial No. 133,733 filed Dec. 16, 1987 we describe a process for making trialkylamines by reacting an alcohol with a mono- or dialkylamine in contact with a catalyst consisting essentially of (1) copper or copper oxide, (2) zinc or zinc oxide and (3) an alkaline earth metal base, e.g. $BaCO_3$. We have now discovered that the process is greatly improved if at least part of one or both of the copper and zinc compounds is initially in the form of a carbonate. Although it is preferred that both the copper and zinc be in the form of carbonates, this is not essential to the achievement of at least part of the improvement made available by the present invention.

The copper component can initially be in the form of a copper carbonate (e.g. $CuCO_3$ calcite, $CuCO_3 \cdot Cu(OH)_2$ malachite, $2CuCO_3 \cdot Cu(OH)_2$ azurite, $Cu_2CO_3$ and the like) or in the form of a copper oxide (e.g. $CuO$, $Cu_2O$, and the like) or mixtures of carbonates and oxides.

The zinc component can initially be in the form of zinc carbonate, $ZnCO_3$ Smithsonite, or in the form of zinc oxide, $ZnO$, or mixtures of zinc carbonate, zinc hydroxide and/or zinc oxide, or in the form of complex hydroxide-carbonates of zinc such as zinc subcarbonate, $3Zn(OH)_2 \cdot 2ZnCO_3 \cdot 4H_2O$, which is mis-identified as "$5ZnO \cdot 2 CO_3 \cdot 4H_2O$" by AlfaProducts and the Merck Index, Sixth Edition but corrected in the Tenth Edition.

The major (i.e. at least 50 weight percent) portion of either the copper or zinc component must initially be in the form of a carbonate. During the reaction, these may decompose or be reduced due to the reaction environment but the process improvement will be achieved in any event as long as the initial state is correct.

In a more preferred embodiment, a major portion of both the copper and the zinc are initially in the form of a carbonate. Most preferably substantially all of the copper is initially a copper carbonate and substantially all of the zinc is a zinc carbonate including complex carbonates.

The third catalyst component is a Group IIA metal base, e.g. oxide, hydroxide, carbonate or mixtures thereof. The preferred Group IIA metals are barium, calcium and magnesium. The most preferred Group IIA metal is barium, most preferably barium carbonate.

The catalytic components can be introduced as separate compounds or as a single composite. For example the catalyst will form in situ by separately adding copper carbonate, zinc carbonate and barium carbonate. Alternatively the catalyst components may be premixed or manufactured in a single process to form a complex intimate composite of all three components.

The catalysts may be unsupported or supported on a material such as alumina, silica, kieselguhr, synthetic or natural zeolite and the like. The catalyst components can be mixed with the powdered support and agglomerated, extruded or pilled by conventional methods. Most preferably the catalyst is used unsupported.

The atom ratio of copper:zinc:Group IIA metal can vary widely. A useful range of atom ratios is 10–100 copper:10–100 zinc:0.02–40 Group IIA metal. More preferably the atom ratio is 10–30 copper:10–30 zinc: 0.1–10 Group IIA metal and most preferably 20:20:1.

The amount of catalyst in the reaction should be a catalytic amount. This means an amount that will catalyze the reaction of the alcohol or aldehyde with the amine to alkylate the amine. The amount of catalyst is expressed in terms of weight percent total catalytic metal based on the weight of the reaction mixture. A useful range is about 0.001–25 weight percent. A more preferred amount of catalyst is 0.05–7 weight percent and a most preferred amount of catalyst is 1–5 weight percent.

The catalyst can be recovered at the completion of the process by settling and/or filtration. Filtration rate is improved by including an inert filter aid such as Celite TM diatomaceous earth in the reaction mixture. The recovered catalyst may be recycled without further treatment and without noticeable loss of activity.

The reaction is preferably conducted in the presence of hydrogen during at least a portion of the reaction. As mentioned earlier the hydrogen can be sparged into the reaction liquid phase together with the di-lower alkylamine (e.g., dimethylamine). The amount or rate of hydrogen sparge does not appear to be critical and indeed the alkylation will proceed without hydrogen sparge albeit at a slower rate. A useful hydrogen sparge rate is 0.001–1000 moles of hydrogen per hour per mole of alcohol. The hydrogen sparge can be used intermittently or continuously during the alkylation. The hydrogen can be diluted with an inert gas such as nitrogen. In one embodiment, hydrogen or a mixture of hydrogen and nitrogen are injected at the start of the reaction to activate the catalyst and then the hydrogen stopped while the nitrogen sparge is started or continued to assist in water removal. If the reaction rate decreases additional hydrogen can be added to the di-lower alkylamine sparge either continuously or periodically to reactivate the catalyst. An especially preferred embodiment of the invention is a process for making $C_{8-22}$ alkyl dimethylamine, said process comprising, (A) mixing a catalyst consisting essentially of a copper carbonate, zinc carbonate and a Group IIA metal base with a $C_{8-22}$ primary mainly straight chain alcohol (B) contacting the mixture of alcohol and catalyst with hydrogen while heating to a reaction temperature of about 180°–250° C.

(C) adding dimethylamine to the mixture of alcohol and catalyst in the continued presence of hydrogen while at said reaction temperature in an amount sufficient to convert at least 95 percent of said alcohol to $C_{8-22}$ alkyl dimethylamine and (D) recovering said $C_{8-22}$ alkyl dimethylamine.

Another especially preferred embodiment of the invention is a process for making a di-($C_{6-20}$ alkyl)methylamine, said process comprising:

(A) mixing a catalyst consisting essentially of a copper carbonate, zinc carbonate and a Group IIA metal base with a $C_{6-20}$ primary mainly straight chain alcohol (B) contacting the mixture of alcohol and catalyst with hydrogen while heating to a reaction temperature of about 180°–250° C.

(C) adding methylamine to the mixture of alcohol and catalyst in the continued presence of hydrogen while at said reaction temperature in an amount sufficient to convert at least 95 percent of said alcohol to di-($C_{6-20}$ alkyl) methylamine and (D) recovering said di-($D_{6-22}$ alkyl) methylamine.

In these especially preferred embodiments the catalyst is mixed with the alcohol before the catalyst contacts the amine. The alcohol catalyst mixture is then heated rapidly to reaction temperature, about 180°–250° C., while contacting the mixture with hydrogen. This serves to activate the catalyst. Once in this activated state the amine reactant can be added without degrading the activity of the catalyst. Contact of the catalyst with amine prior to hydrogen activation has been observed to sharply curtail the reaction rate.

The following examples show how the process can be conducted and the results achieved.

EXAMPLE 1

In a reaction vessel were placed 100 g 1-octadecanol (molten), 1.55 g $CuCO_3$ (J. T. Baker Co., 56.3% Cu), 1.55 g zinc subcarbonate, $5ZnO \cdot 2CO_2 \cdot 4H_2O$ (Alfa Products) and 0.2 g BaCO$_3$. The vessel was flushed with nitrogen and then a hydrogen sparge into the liquid phase was started at 0.1 ft$^3$/hr. The stirred mixture was heated to 210° C. Then a mixed gas sparge of 0.1 ft$^3$/hr hydrogen and 0.4 ft$^3$/hr dimethylamine (DMA) was started. The vent gas was passed through a condenser to remove water and DMA. The reaction was continued for 2 hours at 210° C. with hydrogen and DMA sparge. DMA sparge was then stopped and the mixture cooled to 40° C. Then 2.3 g filter aid (Dicalite TM 4200) was added and the mixture filtered through 1 micron paper. The product was analyzed by gas chromatography (GC) and the results are given in Table I.

EXAMPLE 2

In a reaction vessel were placed 100 g 1-octadecanol (molten) and the recovered catalyst and filter aid from Example 1. The vessel was flushed with nitrogen and then a hydrogen sparge was started at 0.1 ft$^3$/hr. The stirred mixture was heated to 210° C. The sparge was then changed to 0.1 ft$^3$/hr hydrogen and 0.4 ft$^3$/hr DMA. After 2 hours the DMA sparge was stopped and the mixture cooled to 40° and filtered. Product analysis is shown in Table I.

EXAMPLE 3

For comparative purposes the following reaction was conducted using a CuO-ZnO-BaCO$_3$ catalyst.

In a reaction vessel were placed 100 g 1-octadecanol (molten), 1.00 g CuO, 1.00 g ZnO and 0.20 g BaCO$_3$. The vessel was flushed with nitrogen and then a hydrogen sparge at 0.1 ft$^3$/hr was started. The mixture was heated while stirring to 210° C. and the sparge changed to 0.1 ft$^3$/hr hydrogen and 0.4 ft$^3$/hr DMA. Samples were taken periodically and the reaction composition is shown in the following Table I.

TABLE I

| | Reaction Time (hrs) | Percent Octadecyl-dimethylamine | Percent Amide[1] | Percent Heavy[2] Ends |
|---|---|---|---|---|
| Example 1 | 2 | 95.3 | 0.1 | 0.2 |
| Example 2 | 2 | 94.5 | 0.3 | 0.3 |
| Example 3 | 2 | 20.33 | 0.2 | 1.5 |
| | 4 | 46.2 | 0.7 | 3.6 |
| | 8 | 80.0 | 1.3 | 6.9 |

These results show that the addition of copper carbonate and zinc carbonate in combination with barium carbonate give a much faster reaction rate and leads to a high yield of the desired product with very little heavy ends.

The following two examples show the results obtained when only one of the copper or zinc compounds is added as a carbonate and the other is added as an oxide.

EXAMPLE 4

In a reaction vessel were placed 100 g 1-octadecanol (molten), 1.55 g CuCO$_3$, 1.00 g ZnO and 0.2 g BaCO$_3$. The vessel was flushed with nitrogen and then a hydrogen sparge into the liquid phase was started at 0.1 ft$^3$/hr. The stirred mixture was heated to 210° C. at which time the sparge was changed to 0.1 ft$^3$/hr hydrogen and 0.4 ft$^3$/hr DMA. Samples were taken periodically and analyzed by GC. The reaction was continued until conversion of alcohol to a different compound was 99 percent (5 hours). Results are shown in Table II.

TABLE II

| Example 4 Initial Catalyst | Time (hrs) | Octadecyl-dimethylamine | Amide | Heavy Ends |
|---|---|---|---|---|
| CuCO$_3$ / ZnO / BaCO$_3$ | 2 | 57.1% | 1.4% | 5.8% |
| | 5 | 85.7% | 2.0% | 5.1% |

These results show that the use of copper carbonate in combination with zinc oxide and a Group IIA metal base gives a faster reaction rate compared to the use of copper oxide in combination with zinc oxide and the same Group IIA metal base (cf. Example 3) but gives only a small reduction in heavy ends.

EXAMPLE 5

This experiment was conducted in the same manner as Example 4 except the initial catalyst was 1.00 g CuO, 1.55 g zinc subcarbonate (Alfa Products) and 0.2 g BaCO$_3$. Reaction time to 98% alcohol conversion was 4 hours. The results are shown in the Following Table III.

TABLE III

| Example 5 Initial Catalyst | Time (hrs) | Octadecyl-dimethylamine | Amide | Heavy Ends |
|---|---|---|---|---|
| CuO / ZnCO$_3$ / BaCO$_3$ | 2 | 78.3% | 0.2% | 0.7% |
| | 4 | 96.0% | 0.2% | 0.9% |

These results show that merely replacing the initial zinc oxide with zinc carbonate gives a large increase in selectivity to the desired product, octadecyl dimethylamine, and at the same time gives very low amounts of heavy ends. The reaction rate is not as high as when both copper and zinc are added as carbonates.

The following example shows the process used to make a di-higher alkyl monomethylamine.

EXAMPLE 6

In a reaction flask were placed 600 g 1-decanol, 9.3 g CuCO$_3$, 9.3 g zinc subcarbonate (zinc carbonate-hydroxide complex) and BaCO$_3$. The flask was flushed with nitrogen and then sparged with hydrogen (0.7 cf/hr) while heating to 200° C. The sparge was then changed to 0.1 cf/hr hydrogen and about 4 g/min of gaseous monomethylamine. After 2 hours the methylamine feed was stopped and the reaction mixture sampled and analyzed. GC indicated depletion of 1-decanol. At 3 hours an additional 192 g of 1-decanol was added as the amount calculated necessary to react with the dodecylmethylamine in the flask. Reaction was then continued at 200° C. with hydrogen sparge to 4 hours total reaction time. The mixture was cooled and analyzed by GC as follows:

| | |
|---|---|
| didodecylmethylamine | 85 weight percent |
| unsaturated didodecylmethylamine | 3 weight percent |
| dodecylmethylamine | 0.9 weight percent |
| 1-decanol | 1.3 weight percent |
| heavy ends | 0.9 weight percent |

We claim:

1. A process for making a trialkylamine by reacting an alcohol or aldehyde with mono- or dialkylamine at 150°–275° C. in the presence of hydrogen and in contact with a recyclable catalyst initially consisting essentially of (1) a copper compound selected from copper carbonate, copper oxide or copper hydroxide or mixtures thereof, (2) a zinc compound selected from zinc carbonate, zinc oxide or zinc hydroxide or mixtures thereof and (3) a metal compound selected from carbonates, oxides and hydroxides of Group IIA metals or mixtures thereof, at least a portion of at least one of said copper compound and zinc compound initially being introduced as a carbonate, said catalyst being in a solid form and easily separatable from the reaction product by filtration.

2. A process of claim 1 wherein said Group IIA metal compound is barium.

3. A process of claim 1 conducted at 190°–230° C. wherein said zinc compound is a zinc carbonate.

4. A process of claim 3 wherein said copper compound is a copper carbonate.

5. A process of claim 4 wherein said metal compound is barium carbonate.

6. A process of claim 1 wherein said alkylamine is a di-$C_{1-2}$ alkylamine.

7. A process of claim 1 wherein said alcohol or aldehyde is a primary mainly linear alcohol containing about 8–22 carbon atoms or mixtures thereof.

8. A process of claim 7 wherein said alkylamine is dimethylamine.

9. A process of claim 8 conducted at 190°–230° C. wherein said zinc compound is a zinc carbonate.

10. A process of claim 9 wherein said copper compound is a copper carbonate.

11. A process of claim 10 wherein said metal compound is barium carbonate.

12. A process of claim 11 wherein said alcohol is selected from 1-dodecanol, 1-tetradecanol, 1-hexadecanol, 1-octadecanol or 1-eicosanol.

13. A process of claim 1 wherein said alkylamine is a mono-$C_{1-2}$ alkylamine.

14. A process of claim 13 wherein said alcohol or aldehyde is a primary mainly linear alcohol containing 6–20 carbon atoms or mixtures thereof.

15. A process of claim 14 wherein said alkylamine is methylamine.

16. A process of claim 15 conducted at 190°–230° C. wherein said zinc compound is a zinc carbonate.

17. A process of claim 16 wherein said copper compound is a copper carbonate.

18. A process of claim 17 wherein said metal compound is barium carbonate.

19. A process of claim 18 wherein said alcohol is selected from 1-hexanol, 1-octanol, 1-decanol, 1-dodecanol or mixtures thereof.

20. A process of claim 1 wherein said catalyst initially consists essentially of an unsupported mixture of copper carbonate, zinc subcarbonate and barium carbonate.

* * * * *